(12) United States Patent
Evans et al.

(10) Patent No.: US 7,067,122 B1
(45) Date of Patent: Jun. 27, 2006

(54) **MODIFIED LIVE *EDWARDSIELLA TARDA* VACCINE FOR AQUATIC ANIMALS**

(75) Inventors: Joyce J. Evans, Chestertown, MD (US); Phillip H. Klesius, Auburn, AL (US); Craig A. Shoemaker, Notasulga, AL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 19 days.

(21) Appl. No.: 10/858,882

(22) Filed: Jun. 2, 2004

(51) Int. Cl.
*A01N 63/00* (2006.01)
(52) U.S. Cl. ............... 424/93.4; 424/93.2; 424/234.1; 435/243; 435/252.1; 435/261

(58) Field of Classification Search ............. 424/234.1, 424/93.2, 93.4; 435/243, 252.1, 261
See application file for complete search history.

(56) References Cited

U.S. PATENT DOCUMENTS

| 6,019,981 A | 2/2000 | Klesius |
| 6,153,202 A | 11/2000 | Klesius |

*Primary Examiner*—Jennifer Graser
(74) *Attorney, Agent, or Firm*—John D. Fado; Randall E. Deck; Lesley Shaw

(57) ABSTRACT

A safe and effective live vaccine against *Edwardsiella tarda* in fish was created through the induction of rifampicin resistance in a native *Edwardsiella tarda* isolate. Single immersion exposure or injection of fish stimulated acquired immunity against virulent *E. tarda* infection.

9 Claims, No Drawings

MODIFIED LIVE *EDWARDSIELLA TARDA* VACCINE FOR AQUATIC ANIMALS

BACKGROUND OF THE INVENTION

1. Field of the Invention

This invention relates to a novel vaccine against edwardsiellosis which does in fact provide superior protection over commercial treatment involving feeding medicated feeds.

2. Description of the Prior Art

*Edwardsiella tarda* is a Gram-negative, motile, rod shaped, aquatic bacterial pathogen which is highly infectious in both warm and cold water species of fish. The bacterium is commonly encountered in channel catfish ponds, intensive tilapia culture, and eel production systems and is, therefore, a constant threat of disease. In the channel catfish (*Ictalurus punctatus*), it is the causative agent of *Edwardsiella* septicemia disease, and has been isolated from channel catfish in areas of the southeastern United States where this species is cultured. The disease also affects numerous other cultured fish species, sport fish (e.g., largemouth bass), baitfish, and aquarium fishes. Wyatt et al. (1979*, Edwardsiella tarda* in freshwater catfish and their environment, Applied Environmental Microbiology, 38:710–714) found that in *E. tarda* positive catfish ponds, this bacterium was isolated from 75% of the pond water, 64% of pond mud, and 100% of apparently healthy frog, turtle, and crayfish samples. Meyer and Bullock [1973*, Edwardsiella tarda*, a new pathogen of channel catfish (*Ictalurus punctatus*), Applied Microbiology, 25:155–156] highlighted the food safety problem of *E. tarda* when they reported that 88% of dressed catfish were culture-positive for *E. tarda*. This situation usually results in a shut down of the processing lines until they are cleaned and disinfected. Finally, Plumb (1999, Health Maintenance and Principal Microbial Diseases of Cultured Fishes, Iowa State University Press, Ames, Iowa) recommended that care be given to handling *E. tarda* infected fish because of the potential risk of human infection. Edwardsiellosis is also known to affect tilapia culture in both fresh and marine waters.

Medicated feed containing antibiotics is currently used to try and control this bacterial infection. However these treatments are limited in their effectiveness and most producers have discontinued their use. Prevention of edwardsiellosis disease by vaccination is an important goal and a top priority of catfish and other fish producers throughout the world. Estimated savings to these and other industries would be in excess of millions of dollars annually. The considerable economic value of tilapia (Marine Fisheries Service, Fisheries Statistics and Economic Division report, April, 2003) and significant disease losses caused by *E. tarda* dictate the need for an effective *E. tarda* vaccine.

Killed *E. tarda* vaccines have been experimentally produced (Gutierrez, M. A. and Miyazaki. T., 1994, Response of Japanese eels to oral challenge with *Edwardsiella tarda* after vaccination with formalin-killed cells or lipopolysaccharide of the bacterium, Diseases of Aquatic Organisms, 6:110–117) but are not commercially available. Based on the success of disease control by immunization with killed bacteria (i.e., bacterins) in salmonids, experimental bacterins have been developed and tested against *E. tarda* (Salati, F., 1988, Vaccination against *Edwardsiella tarda*, In: Fish Vaccination, edited by A. E. Ellis, Academic Press, London, pp. 135–151). However, no vaccine is currently available and vaccination is not practiced in the catfish industry against *E. tarda*, presumably because the inactivation (i.e., formalin treatment) destroys the antigen. Wolf-Watz et al.

(U.S. Pat. No. 5,284,653) disclosed that a wide variety of bacteria have the potential to be genetically modified to produce a vaccine. However, no data are presented on *E. tarda* vaccines, only on genetically modified mutant vaccines of *Vibrio anguillarum.*

We previously developed a rifampicin resistant vaccine isolate of *Edwardsiella ictaluri* which was effective as a vaccine against this bacterium, a causative agent of enteric septicemia of catfish (RE-33 or Intervet AQUAVAC-ESC) (Klesius, P. and Shoemaker, C.A., 1999, Development and use of modified live *Edwardsiella ictaluri* vaccine against enteric septicemia of catfish, In: Advances in Veterinary Medicine, Vol. 41, edited by R. D. Schultz, Academic Press, San Diego, Calif., pp. 523–537). However, this vaccine is not protective against *E. tarda* infection in channel catfish.

SUMMARY OF THE INVENTION

We have now discovered a novel rifampicin resistant strain of *Edwardsiella tarda* which is a safe and effective live vaccine for the control of *E. tarda* infections in a variety of fish species. The strain of the invention was created by multiple passages of a strain of *E. tarda* (ARS-ET-04) isolated from striped bass, on increasing concentrations of rifampicin supplemented media. The resultant rifampicin-resistant vaccine mutant, which has been designated ARS-RET-04 (NRRL B-30305), is effective in providing long lasting acquired immunity against *E. tarda* in channel catfish and other fish.

In accordance with this discovery, it is an object of this invention to provide a novel, effective vaccine against *Edwardsiella tarda* for fish.

Another object of this invention is to provide an effective vaccine against *E. tarda* which may be administered by injection or bath immersion.

An additional object of this invention is to provide an attenuated *E. tarda* vaccine that is safe and provides long lasting acquired immunity in fish to edwardsiellosis disease, including channel catfish.

A further object of this invention is to improve the viability and productivity of catfish, and to reduce economic losses in the fish industry caused by edwardsiellosis disease.

Other objects and advantages of the invention will become readily apparent from the ensuing description.

DEPOSIT OF BIOLOGICAL MATERIAL

A rifampicin-resistant attenuated *E. tarda* isolate designated ARS-RET-04, was deposited on Jun. 20, 2000 under the provisions of the Budapest Treaty in the Agricultural Research Service Culture Collection (NRRL), 1815 N. University St., Peoria, Ill. 61604, USA, and has been assigned Deposit Accession No. NRRL B-30305.

As used herein, *Edwardsiella tarda* refers to the recognized species, the characteristics of which are described in Bergey's Manual of Determinative Bacteriology (Holt et al., 1994, the contents of which are incorporated by reference herein), and *E. tarda* type strain CDC 148359 (which has been deposited at the American Type Culture Collection, Manassas, Va., USA, as deposit accession number ATCC 15947).

DEFINITIONS

"Vaccine" is defined herein in its broad sense to refer to any type of biological agent in an administrable form capable of stimulating a protective immune response in an animal inoculated with the vaccine. For purposes of this invention, the vaccine comprises a live, attenuated mutant of *E. tarda* having the characteristic of rifampicin-resistance.

Rifampicin, also known as rifampin, refers to 3-[4-methylpiperazinyl-iminomethyl] rifamycin SV (Sigma Chemical Company, St. Louis, Mo.).

The term "revertant" is intended to refer to a subculture of an attenuated bacterium, the subculture being characterized by increased virulence and increased in vivo replication as compared to the attenuated form. The term is used herein generically to encompass both true revertants and apparent revertants, the latter being derived from an existing bacterial population.

DETAILED DESCRIPTION OF THE INVENTION

The present invention provides a novel, highly protective, live vaccine against *Edwardsiella tarda* in fish. The vaccines are effective for controlling infection of fish by any strain of *E. tarda*, including strains which are different from those used in the preparation of the vaccine. Moreover, this vaccine is superior to experimental killed *E. tarda* vaccines because it produces both antibody and cellular immunities, can be administered by more cost-effective bath immersion as well as by injection, and can provide years of protection, instead of only months.

The vaccines of this invention are also effective in controlling infection by *E. tarda* in a variety of fish when administered thereto. Without being limited thereto, the vaccine is especially beneficial for the treatment of American, European, and Japanese eels (*Anguilla* sp.), salmonids (*Oncorhynchus* sp. and *Salmo* sp.), tilapia (*Oreochromis* sp.), striped bass and hybrid-striped bass (*Morone chrysops*× *M. saxatilis*), flounders (*Seriola* sp.), seabream (*Sparus* sp.), sea perch (*Lates calcarifer*), and the estuarine grouper (*Epinephelus tawine*), walleye (*Stitzostedion vitreum*), channel catfish (*Ictalurus punctutus*), centrachids (such as largemouth bass, *Micropterus salmoides*), brown bullheads (*Nebulosus* sp.), bait minnows (*Pimephales promelas*), golden shiners (*Netemigonus crysoleucas*), goldfish (*Carassius auratus*), carp (*Cyprinus carpio*), and aquarium fish species such black mollies (*Poecilia sphenops*) and platies (*Xiphophorus maculatus*). The use of this modified live *E. tarda* vaccine offers several benefits that include reducing disease loss in fresh and marine water fish and eel production, diminishing the food safety risks to humans, and reducing the contamination of water by *E. tarda* that may be discharged in the environment from fish production systems.

The rifampicin resistant strain of *E. tarda* of this invention was created by the multiple passaging of a strain of *E. tarda* (designated ARS-ET-04) which had been isolated from striped bass. As described in detail in Example 1, serial passage of this isolate over increasing concentrations of rifampicin (from 5 to 320 μg/mL) produced a strain, designated ARS-RET-04, with an attenuated pathogenicity efficacious for the preparation of live vaccines. The attenuation achieved by this high-level serial passage in culture on increasing concentrations of rifampicin virtually eliminated the pathogenicity of the bacterium toward fish. This resultant attenuated, rifampicin resistant mutant, no longer possessed the ability of its parent strain of causing the disease state known as edwardsiellosis in catfish and tilapia.

To produce large amounts of the rifampicin resistant mutant *E. tarda* strain ARS-RET-04 for preparation of the vaccine, the bacterium may be cultivated under any conventional conditions and on media which promote growth of *E. tarda*. Without being limited thereto, the strain may be grown on a variety of solid or liquid media types, including but not limited to Helellea agar or tryptic soy agar. The cultures are typically incubated at approximately 25–30° C. for a period of time sufficient to produce maximum levels of cells, generally at least 24–48 hours. In the alternative to growth on solid media, it is also envisioned that the strain may be grown in liquid culture. Without being limited thereto, conventional tryptic soy broth is preferred. The production of the vaccine in this manner may be conducted by stationary culture of the strain at 25–30° C. for 5 to 7 days. All-vegetable based fermentation media are also preferred for use herein, as the use thereof eliminates the risks of the presence of animal products and infectious agents in the final vaccine product.

Following completion of the propagation, the resultant culture of *E. tarda* strain ARS-RET-04 may be recovered for use as a vaccine. Cells, particularly those produced by liquid culture, may be optionally concentrated, for example, by centrifugation or filtration. As a practical matter, it is envisioned that commercial formulations of the vaccine, particularly those to be administered by bath immersion, may be prepared directly from the culture, thereby obviating the need for any purification steps.

Live cells of the *E. tarda* strain are prepared for administration by formulation in an immunologically effective amount or dosage to the fish. The dose may further include pharmaceutically acceptable carriers and adjuvants known in the art. An immunologically effective amount or dosage is defined herein as being that amount which will induce complete or partial immunity (elicit a protective immune response) in a treated fish against subsequent challenge with virulent strain of *E. tarda*. Immunity is considered as having been induced in a population of treated animals when the level of protection for the population (evidenced by a decrease in the number of infected fish or a decrease in the severity of infection) is significantly higher than that of an unvaccinated control group (measured at a confidence level of at least 80%, preferably measured at a confidence level of 95%). Without being limited thereto, in a preferred embodiment, a positive vaccination effect is indicated by a 20% or greater decrease in mortality in the vaccinated population of fish compared to the non-vaccinated control fish population. The appropriate effective dosage can be readily determined by the practitioner skilled in the art by routine experimentation. Although, the vaccine may contain levels as low as about $5\times10^5$ cells (CFU) of *E. tarda*/mL of bath medium, in the preferred embodiment, the vaccine will contain about $1\times10^8$ cells (CFU) of *E. tarda*/mL of bath medium. Depending on fish size, for an intraperitoneal (IP) injection routine, a preferred dose in a fish would be about 0.1 mL of $1\times10^6$ CFU/fish. Although greater amounts of cells may be administered, use of such higher levels is generally considered impractical.

As noted above, the cells may be formulated in an optional, pharmaceutically acceptable carrier such as water, physiological saline, mineral oil, vegetable oils, aqueous sodium carboxymethyl cellulose, or aqueous polyvinylpyrrolidone. The vaccine formulations may also contain optional adjuvants, antibacterial agents or other pharmaceutically active agents as are conventional in the art. Without being limited thereto, suitable adjuvants include but are not limited to mineral oil, vegetable oils, alum, and Freund's incomplete adjuvant. Still other preferred adjuvants include microparticles or beads of biocompatible matrix materials. The microparticles may be composed of any biocompatible matrix materials as are conventional in the art, including but not limited to, agar and polyacrylate. The practitioner skilled in the art will recognize that other carriers or adjuvants may be used as well. For example, other adjuvants which may be used are described by Webb and Winkelstein [in Basic & Clinical Immunology, Stites et al. (ed.), fifth edition, Lange Medical Publications, Los Altos, Calif., 1984, pages 282–285], the contents of which are incorporated by reference herein.

The vaccines of the invention may be administered to the subject animal by any convenient route which enables the cells to elicit an immune response, such as by IP or intramuscular injection, bath immersion, oral administration, or nasal administration. However, IP injection or bath immersion is preferred for primary immunization, while oral immunization is preferred for secondary or booster immunization, when necessary. It is also envisioned that the surface of the fish may be punctured such as described by Nakanishi et al. (2002, Development of a new vaccine delivery method for fish: Percutaneous administration by immersion with application of a multiple puncture instrument, Vaccine, 20:3764–3769) or otherwise abraded or slightly descaled, prior to or during bath immersion, to facilitate exposure of the vaccine to the animal's immune system. The vaccine may be administered in a single dose or in a plurality of doses. Dependent upon rearing conditions, the vaccine may be administered in multiple doses, the timing of which may be readily determined by the skilled artisan.

Vaccination against infection by *E. tarda* by bath immersion immunization offers several advantages over other routes of immunization. Among these advantages are lower cost per fish immunized, mass immunization of large numbers of fish, reduced stress, significantly higher rates of fish survival and the absence of adverse reactions to vaccination. Furthermore, bath immersion vaccination is an effective method for mass vaccination of smaller fish that can not be injected or subjected to skin punctures. Alternatively, IP injection of commercially available fish vaccines is commonly employed on fresh or marine aquaculture farms due to their reliability and high efficacy despite high cost per fish immunized and stress to the fish.

In a preferred embodiment, the vaccine is administered to 7–10 day old fish and eels by bath immersion, injection, and/or any oral delivery or immersion device. Typically, fish are vaccinated by immersion in water containing about $1 \times 10^6$ to $1 \times 10^7$ CFU/mL of the attenuated *E. tarda* for 30 minutes at a density of about 40 fish/L and a temperature of about 26° C. Fish may also be vaccinated with $1 \times 10^6$ CFU/mL of *E. tarda* mutant by intraperitoneal injection (IP). Suitable vaccination times may range from about 1 minute to about 30 minutes, preferably from about 2 minutes to about 15 minutes. The temperature of the inoculation media may range within the physiologically acceptable limits of the fish involved, for channel catfish preferably from about 18° C. to about 28° C., most preferably from about 22° C. to about 28° C. Concentrations of fish treated in the inoculation medium typically range from about 50 to about 100 fish/L, but, in the alternative, be determined on a weight basis and range from about 0.5 to about 2.5 kg/L. The vaccine can be effectively administered anytime after the fish attains immunocompetence, which for channel catfish is at about the second day to fourteen days post-hatch. Other species of fish susceptible to *E. tarda* can be immunized after 21–30 days post-hatch or when they become immunocompetent to modified live vaccine administered by immersion.

The following examples are intended only to further illustrate the invention and are not intended to limit the scope of the invention which is defined by the claims.

EXAMPLE 1

The procedure used to produce the *E. tarda* vaccine mutants was modified from that described in Shurig et al. (1991, Vet. Micro. 28:171–188, the contents of which are incorporated by reference herein), by using a lower initial concentration of rifampicin, 5 µg/mL, ending at 320 µg/mL after 64 passages instead of 51 passages, and omitting the penicillin step.

Process of Developing Resistant Mutants of *Edwardsiella tarda*

Tryptic Soy Agar (TSA) plates for the cultivation of *E. tarda* were made according to the procedure of Klesius et al. (1999, Effect of feed deprivation on innate resistance and antibody response to *Flavobacterium columnare* in channel catfish, *Ictalurus punctatus*, Bulletin European Association of Fish Pathologists, 19(4):156–158). Forty g soybean-casein digest agar was added to 1 L of distilled water (Becton Dickinson, Sparks, Md.), and heated until dissolution. The media was then autoclaved at 121–124° C. for 15 minutes, poured into sterile petri dishes (15 mL per dish), and allowed to solidify before refrigeration.

Isolates of *E. tarda* for use herein were obtained from sick fish or previously obtained lyophilized stocks (Table 1), and included *E. tarda* strain ARS-ET-04 (FL6-60). The isolates were identified as *E. tarda* by standard biochemical tests as set forth in Bergey's Manual of Determinative Bacteriology prior to their use to develop rifampicin resistant mutants. Rifampicin resistant mutants of *E. tarda* were developed using rifampicin supplemented modified TSA plates prepared as follows: modified TSA was made as described above and sterilized at 121–124° C. for 15 minutes. After sterilization, the correct amount of rifampicin (3-[4-methylpiperazinyl-iminomethyl] rifamycin SV) (Sigma Chemical Company, St. Louis, Mo.) was added to the media prior to its solidification and 15 mL of the resulting mixture was poured into separate petri dishes and allowed to solidify prior to refrigerated storage.

Initial cultures of the *E. tarda* isolates were grown on modified TSA which were incubated at 20–25° C. for 24–48 hours or until 1–2 mm grayish-white, round colonies were observed. A single *E. tarda* colony was then picked with a sterile inoculating loop and streaked onto a rifampicin supplemented, modified TSA plate containing the correct concentration of the antibiotic. For the initial passage, rifampicin was present in the modified TSA at a concentration of 5 µg/mL. The rifampicin supplemented modified TSA that was streaked with the aforementioned native isolate of *E. tarda* was then incubated for 24–48 hours at 20–25° C. and observed for bacterial growth. Single colonies of *E. tarda* that grew on the rifampicin supplemented media were then picked and placed onto the next concentration of rifampicin (10 µg/mL) modified TSA plates. If growth occurred, a single colony was harvested and placed on an agar media containing the next higher concentration of rifampicin (20 µg/mL). If the harvested colony failed to grow on the 20 µg/mL media, it was repeatedly passed on a media containing the last concentration of rifampicin at which growth successfully occurred (i.e., 10 µg rifampicin/mL), before being placed on 40 µg/mL concentration of rifampicin containing media. This process was repeated at successively higher rifampicin levels (increasing at 20 µg rifampicin/mL increments), until a colony capable of growing on media containing a rifampicin concentration of 320 µg/mL was obtained.

The rifampicin resistant isolate of *E. tarda* was selected from the 64th passage on 320 µg/mL of rifampicin (i.e., one colony from the original passage that grew and was passed). This mutant, which was derived from the afore-mentioned strain ARS-ET-04, was designated *E. tarda* strain ARS-RET-04. The ARS-RET-04 mutant was deposited on Jun. 20, 2000, under the provisions of the Budapest Treaty in the Agricultural Research Service Culture Collection in Peoria, Ill., and was assigned Deposit No. NRRL-B-30305.

Mutant strain ARS-RET-04 is differentiated from the parent microorganism because it can survive and reproduce on a media containing 320 μg rifampicin/mL rifampicin without negative effect. Biochemical characteristics of the *E. tarda* mutant ARS-RET-04 (NRRL B-30305) are identical to its *E. tarda* parent, and are the same as those described for *E. tarda* type strain 148359 (ATCC 15947) as described in Bergey's Manual of Determinative Bacteriology (Holt et al., 1994), the contents of which are incorporated by reference herein.

EXAMPLE 2

Seven additional *Edwardsiella tarda* isolates were examined for their ability to induce rifampicin-resistance at a concentration of 120 μg/mL using the same process as described in Example 1. The additional *E. tarda* isolates (Table 1) were passaged on increasing concentrations (5, 10, 20, 40, 60, 80 and 100 μg rifampicin/mL) supplemented TSA to a final concentration of 120 μg rifampicin/mL. The *E. tarda* isolates were obtained from channel catfish, hybrid striped bass, tilapia, and bluegill with signs of edwardsiellosis disease. The *E. tarda* were cultured on TSA and determined to be pure cultures. Isolates obtained were frozen in 2 mL aliquots at −80° C. Prior to propagation, frozen aliquots were thawed to 25° C., fifty microliters were then plated onto each of the media types (i.e., TSA and TSA supplemented with 5 μg rifampicin/mL and incubated at 25±3° C. for 24 h. The development of grayish-white, round colonies on agar was considered positive for growth. This process was repeated at successively higher rifampicin levels as described in Example 1 up to a rifampicin concentration of 100 μg/mL. Growth was not observed with any of the isolates tested on TSA supplemented with 120 μg rifampicin/mL. All seven of the additional *E. tarda* isolates failed to become rifampicin-resistant at a concentration of 120 μg/mL. Failure of induction of rifampicin resistance was demonstrated by no growth on rifampicin supplemented TSA. The lack of growth on TSA supplemented with 120 μg rifampicin/mL demonstrated that these 7 isolates were not viable candidates for development of modified live *E. tarda* vaccines because rifampicin resistance could not be induced therein (see Table 1). The *E. tarda* isolates tested grew on TSA only with typical *E. tarda* colonies developing.

EXAMPLE 3

Virulence and Rifampicin Resistance in Tilapia

For this experiment, 20 tilapia (*Oreochromis niloticus*) with an average weight of 13.3 grams and average length 91.0 mm were separated into 12 continuous flow tanks at approximately 26° C. The fish were habituated over a 24 h period and fed to satiation with Aquamax Grower 400. Two isolates of *E. tarda*, ARS-RET-04 (Mutant) and ARS-ET-04 parent, were streaked onto sheep blood agar and the plates allowed to incubate for 24 h at 30° C. in an atmosphere of air. A diluting solution of 0.1% peptone water was prepared. After 24 h, the cultures were harvested and the inoculum was matched to McFarland standard 10 (approximately OD 1.4) using a transmittance meter. The inocula were placed in an ice bath in preparation for injection. The number of CFU/mL was determined through a dilution series. Each inoculum was plated at 1:10 dilutions of $10^4$ to $10^7$ on TSA in triplicate using a spiral plater. The plates were incubated at 30° C. for 24 h in air. After 24 h, the colonies were counted using the method of Spiral Biotech and recorded. The average number of CFU/mL was calculated and the CFU to be received by the fish determined. Twenty fish each received 0.1 mL of ARS-RET-04 at concentrations $1\times10^4$, $1\times10^5$, $1\times10^6$, $1\times10^7$, and $1\times10^8$ CFU/mL of and 20 fish each received 0.1 mL of ARS-ET-04 at the same concentrations via intraperitoneal (IP) injection. The fish of each treatment were kept in separate tanks maintained at approximately 26° C. and fed to satiation. The control fish either were not injected (N=20) or IP injected with TSB only (N=20). Fish were observed daily, post injection, for signs of disease.

Following inoculation with the bacteria, fish observed to be moribund or morbid were removed from the tanks. The intestines and head kidneys of the fish were swabbed, streaked onto TSA, and the plates incubated at 30° C. After 24 h of incubation and again at 48 hours, the plates were assessed for growth and the phenotypic characteristics of each group of colonies noted. The results in Table 2 show that ARS-ET-04 parent was virulent. All ARS-RET-04 isolates exhibited resistance to the 320 μg rifampicin/mL indicating that the mutant is still resistant after passing through the fish and that no reversion occurs.

EXAMPLE 4

Efficacy-Immersion

Tilapia (N=240) were vaccinated with *E. tarda* ARS-RET-04 mutant by bath immersion for a 30 minute exposure. The average weight of the fish was 4 grams. Fish were immunized by immersion with $1.0\times10^5$, $1.0\times10^6$, $1.0\times10^7$ and $1.0\times10^8$ CFU/mL of the ARS-RET-04 vaccine mutant in 12 tanks of 20 fish/tank/3 replicates. Sixty tilapia (N=20/tank/3 replicates) were exposed to bath immersion in TSB for 30 minutes to serve as control fish (i.e., non-vaccinated). Vaccinated and control fish were held for 30 days following vaccination before they were challenged with virulent *E. tarda*. The results showed that significant survival was provided in the vaccinated fish (Table 3). The survival in vaccinates at increasing concentration of the ARS-RET-04 mutant administered by immersion was 17, 18, 19, and 22.1% in comparison to 5.2% of the non vaccinated control fish.

Efficacy of Intraperitoneal (IP) Injection

Tilapia (N=225) were vaccinated with *E. tarda* ARS-RET-04 mutant by IP injection. The average weight of the fish was 29.3 grams. Fish were immunized by IP with 0.1 mL of $1.0\times10^6$ and $1.0\times10^7$ CFU/mL of the ARS-RET-04 mutant in 9 tanks of 25 fish/tank/3 replicates. Seventy five tilapia (N=25/tank/3 replicates) were injected 0.1 mL with TSB to serve as control fish (i.e., non-vaccinated). Vaccinated and control fish were held for 30 days following vaccination before they were challenged with virulent *E. tarda*. The results showed that significant survival were provided in the vaccinated fish (Table 4). The survival in vaccinates (ARS-RET-04 mutant) administered 1×10⁷ CFU/mL by IP injection was 39.2% compared to 12.0% in the non-vaccinated control fish. Fish IP vaccinated with 1.0×10⁶ CFU/mL had a survival rate of 27.0%.

EXAMPLE 5

Efficacy Intraperitoneal (IP) Injection in Channel Catfish

Channel catfish (N=90, Goldkist strain) were vaccinated with *E. tarda* ARS-RET-04 mutant by IP injection. The average weight of the fish was 30.0 grams. Fish were immunized 1×10⁶ CFU of *E. tarda* ARS-RET-04/fish. Ninety immunized fish were placed in 3 replicate tanks, held for 30 days and challenged with virulent *E. tarda* ARS-ET-04 at 30 days post-immunization. The results show that vaccination of channel catfish with the *E. tarda* ARS-RET-04 mutant produced a significant increase in survival (Table 5). Fifty percent of the vaccinates survived the challenge infection, whereas only 18.0 percent of the non-vaccinates (controls) survived.

Efficacy Immersion Vaccination in Channel Catfish

Channel catfish (N=550, Goldkist strain) were vaccinated with *E. tarda* ARS-RET-04 mutant by immersion. The average weight of the fish was 30.0 grams. Fish were immunized with *E. tarda* ARS-RET-04 at different vaccine concentrations in one liter immersion exposures. Five hundred and fifty immunized fish were placed in 3 replicate tanks (50 fish/tank) and challenged with virulent *E. tarda* ARS-ET-04 at 30 days post-immunization by immersion. The results show that vaccination of channel catfish with the *E. tarda* ARS-RET-04 mutant produced a significant increase in survival (Table 6). Ninety six percent of vaccinates immunized with 4 mL vaccine per L of bath survived the challenge infection, whereas only 89.0 percent of the non-vaccinates (controls) survived.

It is understood that the foregoing detailed description is given merely by way of illustration and that modification and variations may be made therein without departing from the spirit and scope of the invention.

TABLE 1

Growth of *Edwardsiella tarda* isolates on rifampicin supplemented tryptic soy broth agar.

| Isolate designation[1] | Origin of isolate | Tryptic Soy Broth Agar | Rifampicin Concentrations 120 μg/mL | 320 μg/mL |
|---|---|---|---|---|
| ARS-RET-04 | Striped Bass | Yes | Yes | Yes |
| ARS-ET-04 | Striped Bass | Yes | No | No |
| AL[2]-93-68 B | Channel Catfish | Yes | No | No |
| AL-HSB-K-03 | Hybrid Striped Bass | Yes | No | No |
| AL-BG-32K-03 | Bluegill | Yes | No | No |
| AL-TN-B-03 | Tilapia | Yes | No | No |
| AU[3]-TN-P fluid-03 | Tilapia | Yes | No | No |
| AL-CC-B-02 | Channel Catfish | Yes | No | No |
| ARS[4]-11-8-01 | Channel Catfish | Yes | No | No |

[1]*Edwardsiella tarda* isolates all from fish showing signs of edwardsiellosis disease.
[2]AL = Alabama Fish Farming Center, Greensboro, AL, Case Number.
[3]AU = Auburn University Fisheries and Allied Aquaculture, Isolate Number.
[4]ARS = USDA/ARS/Aquatic Animal Health Research Laboratory Isolate Number.

TABLE 2

Virulence of ARS-ET-04 (Parent) and ARS-RET-04 and rifampicin resistance of ARS-RET-04 following passage through fish.

| Isolate | Dose (CFU/fish) | No. Dead/ No. Total (% Mortality) | Resistance to 320 μg rifampicin/ml Isolate of *E. tarda* from Intestine | Head kidney |
|---|---|---|---|---|
| ARS-ET-04 Parent | $1.0\times10^3$ | 0/20 (0) | No | No |
| ARS-ET-04 | $1.0\times10^4$ | 0/20 (0) | No | No |
| ARS-ET-04 | $1.0\times10^4$ | 0/20 (0) | No | No |
| ARS-ET-04 | $1.0\times10^5$ | 0/20 (0) | No | No |
| ARS-ET-04 | $1.0\times10^6$ | 0/20 (0) | No | No |
| ARS-ET-04 | $1.0\times10^7$ | 11/20 (55) | No | No |
| ARS-RET-04 | $1.0\times10^3$ | 0/20 (0) | Yes | Yes |
| ARS-RET-04 | $1.0\times10^4$ | 0/20 (0) | Yes | Yes |
| ARS-RET-04 | $1.0\times10^4$ | 0/20 (0) | Yes | Yes |
| ARS-RET-04 | $1.0\times10^5$ | 0/20 (0) | Yes | Yes |
| ARS-RET-04 | $1.0\times10^6$ | 0/20 (0) | Yes | Yes |
| ARS-RET-04 | $1.0\times10^7$ | 0/20 (0) | Yes | Yes |
| Control no infection | — | 0/20 (0) | — | — |
| Control TSB only | — | 0/20 (0) | — | — |

TABLE 3

Protection against edwardsiellosis disease after immersion vaccination[1] of tilapia with *E. tarda* ARS-RET-04 vaccine.

| Treatment | No. of fish | Percent Mortality | Percent survival |
|---|---|---|---|
| Vaccinated with ARS-RET-04 mutant | 59 | 77.9 | 22.1 |
| Control (non-vaccinated) | 40 | 94.8 | 5.2 |

[1]Immersion vaccination for 30 minutes with $1\times10^8$ *E. tarda* ARS-RET-04 for 30 minute immersion exposure.

TABLE 4

Protection against edwardsiellosis disease after IP vaccination[1] of Tilapia with *E. tarda* ARS-RET-04 vaccine.

| Treatment | No. of fish | Percent Mortality | Percent survival |
|---|---|---|---|
| Vaccinated with ARS-RET-04 mutant | 75 | 60.8 | 39.2 |
| Control (non-vaccinated) | 74 | 88 | 12.0 |

[1]IP vaccination with $1\times10^6$ *E. tarda* ARS-RET-04 or NRRL B-30305.

TABLE 5

Protection against edwardsiellosis disease after IP vaccination[1] of channel catfish (Goldkist strain) with *E. tarda* ARS-RET-04 vaccine.

| Treatment | No. of fish | Percent mortality | Percent survival |
|---|---|---|---|
| Vaccinated with ARS-RET-04 mutant | 90 | 49.3 | 50.7 |
| Control (non-vaccinated) | 90 | 92.0 | 18.0 |

[1]IP vaccination with $1\times10^6$ CFU of *E. tarda* ARS-RET-04. Challenge with ARS-ET-04 parent by IP injection with $2.4\times10^6$ CFU/fish at 30 days post-vaccination.

TABLE 6

Protection against edwardsiellosis disease after immersion vaccination[1] of channel catfish (Goldkist strain) with *E. tarda* ARS-RET-04 vaccine.

| Treatment | Amount of vaccine mL/1 L bath for 2 minute exposure | No. of fish | Percent mortality | Percent survival |
|---|---|---|---|---|
| Vaccinated with ARS-RET-04 mutant | 2 | 150 | 4.7 | 95.3 |
| Vaccinated with ARS-RET-04 mutant | 4 | 150 | 4.0 | 96.0 |
| Vaccinated with ARS-RET-04 mutant | 6 | 160 | 6.0 | 94.0 |
| Vaccinated with ARS-RET-04 mutant | 8 | 100 | 10 | 90.0 |
| Control (non-vaccinated) | 0 | 150 | 10.7 | 89.3 |

[1]Immersion vaccination with *E. tarda* ARS-RET-04 mL/L for 2 minutes. Challenge with ARS-ET-04 parent by immersio with $2.4 \times 10^6$ CFU/mL/L at 30 days post-vaccination.

We claim:

1. A rifampicin resistant mutant strain of *Edwardsiella tarda* deposit accession no. NRRL B-30305.

2. The rifampicin resistant mutant strain of *Edwardsiella tarda* which is substantially biologically pure.

3. A vaccine composition comprising an immunologically effective amount of a rifampicin resistant mutant strain of *Edwardsiella tarda* deposit accession no. NRRL B-30305.

4. The composition of claim 3 further comprising an inert carrier or diluent.

5. A method for protecting fish against infection by *Edwardsiella tarda* comprising administering the composition of claim 3 thereto.

6. The method of claim 5 wherein said fish is selected from the group consisting of tilapia and channel catfish.

7. The method of claim 6 wherein said fish is channel catfish.

8. The method of claim 5 wherein said composition is administered by intraperitoneal injection or bath immersion.

9. The method of claim 6 wherein said fish is tilapia.

* * * * *